(12) United States Patent  
Liu et al.

(10) Patent No.: US 8,229,070 B2
(45) Date of Patent: Jul. 24, 2012

(54) INTRAFRACTION MOTION MANAGEMENT USING A ROUGH TO ACCURATE MONITORING STRATEGY

(75) Inventors: Wu Liu, New London, CT (US); Lei Xing, Palo Alto, CA (US); Gary Luxton, Mountain View, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 189 days.

(21) Appl. No.: 12/924,171

(22) Filed: Sep. 22, 2010

(65) Prior Publication Data

US 2011/0075807 A1    Mar. 31, 2011

Related U.S. Application Data

(60) Provisional application No. 61/277,977, filed on Sep. 30, 2009.

(51) Int. Cl.
*A61N 5/10* (2006.01)
(52) U.S. Cl. ........................................... 378/65; 378/62
(58) Field of Classification Search .............. 378/62–63, 378/207, 64–65
See application file for complete search history.

(56) References Cited

U.S. PATENT DOCUMENTS

| | | | |
|---|---|---|---|
| 2009/0208074 A1* | 8/2009 | Wiersma et al. | 382/128 |
| 2010/0067739 A1* | 3/2010 | Mostafavi et al. | 382/103 |
| 2010/0119032 A1 | 5/2010 | Yan et al. | |

* cited by examiner

*Primary Examiner* — Hoon Song
(74) *Attorney, Agent, or Firm* — Lumen Patent Firm

(57) ABSTRACT

An adaptive imaging method of monitoring intrafraction target motion during radiation therapy is provided that includes using a simultaneous Mega-Voltage (MV) imaging process and Kilo-Voltage (KV) imaging process to determine an initial 3D target position. 2D target position is monitored using the MV imaging process during a radiation therapy treatment delivery, and is in combination with an online-updated characterization of target motion that are disposed to estimate if the target has moved beyond a 3D threshold distance. The simultaneous MV imaging and KV imaging processes are for accurately determining a new 3D target position for intrafraction motion compensation and for further 2D imaging by the MV imaging process, where another simultaneous MV and KV imaging process is initiated when the target has potentially moved beyond the threshold distance as measured by the MV imaging process. The intrafraction target motion monitoring is achieved at the cost of ultralow patient imaging dose.

12 Claims, 3 Drawing Sheets

INTRAFRACTION MOTION MANAGEMENT USING A ROUGH TO ACCURATE MONITORING STRATEGY

CROSS-REFERENCE TO RELATED APPLICATIONS

This application claims priority from U.S. Provisional Patent Application 61/277,977 filed Sep. 30, 2009, which is incorporated herein by reference.

STATEMENT OF GOVERNMENT SPONSORED SUPPORT

This invention was made with Government support under contract W81XWH-09-1-0180 awarded by ARMY/MRMC. The Government has certain rights in this invention.

FIELD OF THE INVENTION

The current invention relates to intensity-modulated radiotherapy (IMRT). More particularly, the invention relates to an adaptive imaging method monitoring intrafraction target motion during IMRT using MV treatment beam imaging supplemented by minimal as-needed use of on-board kV imaging.

BACKGROUND OF THE INVENTION

Prostate motion management is critical for modern high-conformality dose-escalated prostate intensity-modulated radiotherapy (IMRT). Numerous clinical studies show that, in comparison to skin tattoo or bony anatomy alignment, use of gold markers in conjunction with pre-treatment portal MV or on-board kV imaging can significantly reduce the setup margins and therefore potentially lead to decreased normal tissue toxicity. Intrafraction prostate motion is considered to be a limiting factor on margin reduction, at least for patients with relatively large intrafraction motion. Because intrafraction prostate motion is generally more unpredictable than respiration motion, techniques developed for respiratory motion correction, such as gating based on external surrogates, are often not directly applicable.

Although recently developed electromagnetic transponders provide real-time 3D localization without radiation dose, they are physically much larger than the gold markers conventionally used in radiographic tracking and produce severe MRI artifacts, hindering MR-based post-treatment assessment. Real-time simultaneous acquisition of two X-ray images from different viewing angles for 3D target localization has also been implemented with sub-millimeter accuracy, e.g., fluoroscopic imaging using two kV systems, and MV-kV imaging using cine-MV and fluoroscopic kV systems. Stereoscopic X-ray imaging with one or two kV sources, however, poses the problem of accumulating excessive patient imaging dose. A reliable reduction of kV beam use would be highly desirable.

The prostate is mostly stationary and drifts slowly with abrupt motion occurring only occasionally. What is needed is a minimally invasive method to detect only motion that is potentially beyond a pre-defined threshold. Then assess the over-threshold event and obtain more accurate position information to use for interventional motion correction.

SUMMARY OF THE INVENTION

To address the needs in the art, a method of monitoring intrafraction target motion during radiation therapy is provided. The method includes using a first simultaneous Mega-Voltage (MV) imaging process and Kilo-Voltage (KV) imaging process to determine an initial 3D target position, where the MV imaging process includes a MV imager, and the KV imaging process includes a KV imager. The method further includes monitoring a 2D target position using the MV imaging process during a radiation therapy treatment delivery, where the 2D target position monitoring is in combination with an online-updated characterization of target motion, where the 2D target position monitoring and the online-updated characterization of the target motion are disposed to estimate if the target has moved beyond a 3D threshold distance. Additionally, the method uses the simultaneous MV imaging process and KV imaging process to accurately determine a new 3D target position for intrafraction motion compensation and for further 2D imaging by the MV imaging process, where another simultaneous MV imaging process and KV imaging process is initiated when the target has potentially moved beyond the threshold distance as measured by the MV imaging process, where the intrafraction target motion monitoring is provided at a cost of ultralow patient imaging dose.

According to one aspect of the invention, the MV imaging process is a cine MV imaging process.

In a further aspect of the invention, the motion compensation includes patient repositioning through automatic couch control or use of a dynamic multi-leaf collimator MLC.

In one aspect of the invention, the MV imaging process includes a first viewing angle and the KV imaging process includes a second viewing angle.

In another aspect of the invention, a confirmation request is generated when the target potentially moves beyond the threshold distance based on motion estimation. Here, the simultaneous MV imaging process and KV imaging process is initiated upon the confirmation request to confirm the target has moved beyond the threshold distance. In one aspect, the target is repositioned when the confirmation request is confirmed.

According to another aspect of the invention, the simultaneous MV imaging process and KV imaging process comprises a triangulation imaging of the target.

In another aspect of the invention, anterior-posterior motion is correlated with superoinferior motion of the target.

In a further aspect of the invention, the threshold distance is at least 1 mm.

In yet another aspect of the invention, the KV imager includes an x-ray KV imager.

According to another aspect of the invention, the intrafraction motion tracking includes the MV imager and another imaging modality.

DETAILED DESCRIPTION

The current invention provides a "failure" detection strategy to detect in a first step only motion that is potentially beyond a pre-defined threshold using treatment beam MV imaging, available at no tracking dose cost. The cine MV imaging and correlative relationship between directional components of target motion, for example prostate motion, is used for the first step estimation. In a second step, combined MV-kV imaging is performed by turning on the kV imager to assess the overthreshold event. This step also obtains more accurate position information, which is later used for interventional motion correction. The kV usage is significantly reduced because cine-MV monitoring alone is sufficient during most of the treatment session. This scheme of using the kV imager adaptively (on an "as needed" basis) significantly improves a "one-protocol-for-all-treatment" approach in prostate IGRT.

The current invention provides a MV data processing method that is suitable for the "failure" detection scheme during IMRT by incorporating simple assumptions based on prior knowledge of target motion without introducing complicated statistical models and requiring no pretreatment patient-specific training data.

The current invention provides a method to monitor intrafraction prostate motion without the excessive overhead of continuous kV imaging.

Figure 1:
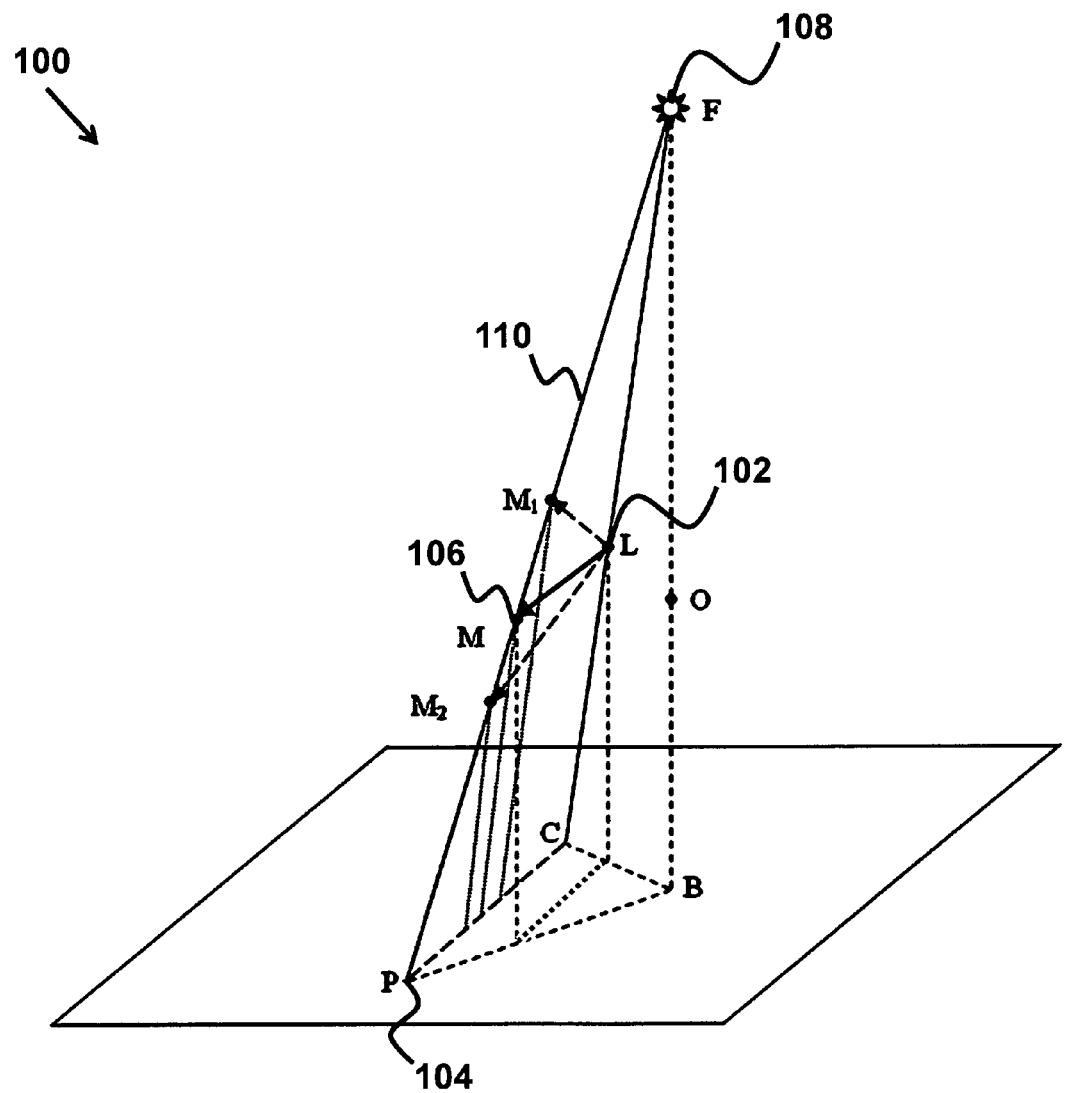
FIG. 1 shows projection geometry for estimating fiducial position based on sequential MV images, according to one embodiment of the invention.

The method of the current invention contains two steps. First, to turn on the kV (for one time or a period of time) only if cine MV-estimation suggest that the target has moved more than a predefined threshold (3 mm) from a previously established checkpoint whose 3D position is known; and then, to update the checkpoint if the MV-kV triangulation confirms that the displacement is more than 2.5 mm. Because of the absence of prior knowledge at the beginning of treatment, the kV imager is turned on one time to acquire the first accurate 3D target checkpoint position. In this section, we will introduce three different, but related methods for detecting potential over-threshold motion in fixed gantry IMRT from cine MV. Referring to FIG. 1, where shown is projection geometry 100 for estimating fiducial position based on sequential MV images. As shown, point "L" 102 is a checkpoint fiducial location, determined by simultaneous MV-kV data. At later times, only cine-MV images are acquired to estimate fiducial displacement from checkpoint L. Point "P" 104 is the projected fiducial position on the current MV image. The 3D fiducial position "M" 106 to be estimated is along the line joining P 104 and the x-ray source "F" 108. Therefore, the fiducial displacement is $$\vec{LM} = \vec{FM} - \vec{FL} = t \cdot \vec{FP} - \vec{FL} \quad (1)$$

where t is a scaling factor to be solved. For the remainder of this exemplary discussion, it is assumed that the treatment table is parallel to the gantry rotation axis.

The invention further includes triggered kV imaging using two-dimensional (2D) MV distance. In one aspect, one method for estimating the fiducial displacement assumes that there is no inline (i.e., perpendicular to imager plane) fiducial motion, between the current time and the time when the checkpoint was imaged, is parallel to the imager. The motion in the superoinferior (SI) direction may then be expressed as $$\Delta SI \approx \vec{CP}_{SI} \cdot \frac{|\vec{FL}|}{|\vec{FC}|} \quad (2)$$

where $\vec{CP}_{SI}$ is the $\vec{CP}$ projected onto the SI direction and C is the projected position of L in the updated MV image. The fiducial position M 106 can be solved using Eq. 1 and 2.

The distance from the fiducial to the isocenter ($\vec{MO}$) is much smaller than the source-to-axis distance ($\vec{FO}$). Therefore the estimated 2D motion parallel to the imager ($\vec{LM}$) is approximately the shortest possible distance from L 102 to the line FP 110.

Figure 2:
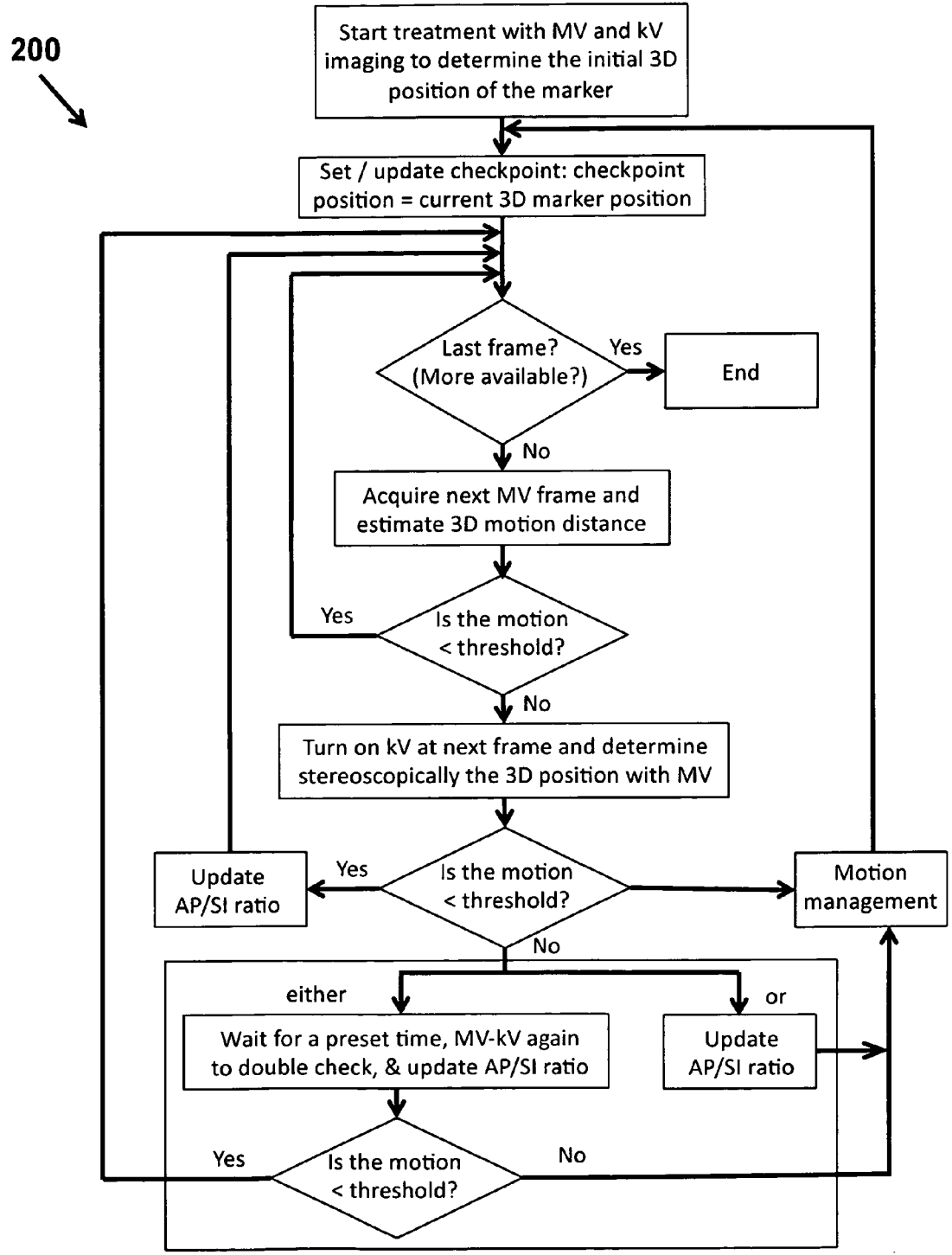
FIG. 2 shows a flowchart of the entire motion monitoring procedure, according to one embodiment of the invention.

The invention further includes triggering kV imaging using estimated 3D MV distance according to prior knowledge. Knowledge of the characteristics of target motion, for example prostate motion, can be readily used to improve 3D motion estimation for overthreshold motion detection. The lateral motion is typically significantly smaller than and independent of the vertical and longitudinal motions and the vertical and longitudinal motions are highly correlated, consistent with the pelvis and prostate anatomy. Because the SI motion is always perpendicular to the plane of gantry rotation, the SI motion can always be reliably measured from cine MV. Considering all the facts above, an estimated inline fiducial motion is added (i.e., the component of anteroposterior (AP) displacement perpendicular to the imager), as follows:

$$\Delta \perp = \eta \cdot \Delta SI \cdot \cos \alpha \quad (3)$$

where $\eta$ is an estimated ratio of AP to SI motion ($\Delta AP = \Delta SI$) and $\alpha$ is the gantry angle relative to the vertical direction. The ratio $\eta$ was updated every time whenever combined data from MV-kV imaging were available. The assumption here is that the ratio does not change significantly during a short period. To avoid the complication of acquiring and being influenced by patient specific training data, no statistical motion model was provided. The reason not to do so is that only detection of potential over-threshold motion is required at this stage, not to determine accurate 3D localization. This estimated inline motion is combined with the calculated in-plane motion as described above to estimate a 3D fiducial displacement. Curve fitting and prediction are provided to estimate the possible 3D displacement at the next frame for use in the next step. The second step of the current motion monitoring method is to trigger kV imaging whenever the estimated 3D displacement is greater than a preset threshold. Whether a checkpoint update (repositioning) is performed or not is determined based on the actual fiducial motion measured from the combined MV-kV data. The ratio of AP to SI motion is updated whenever an MV-kV image pair is taken. FIG. 2 shows a flowchart of the entire motion monitoring procedure.

The current invention includes triggering kV imaging using estimated 3D MV distance with information from a previous IMRT angle "3D+ estimation". The data from the previous treatment angle also provides potential useful information to estimate 3D marker position. In addition to the 3D estimation method, at the beginning of each new gantry angle, 3D marker position is stereoscopically estimated using the current image and last several images from the previous field, assuming no motion between this acquisition and that from the previous gantry angle. If the estimated displacement is larger than the preset threshold (invalidating the no-motion hypothesis), then kV imaging is also triggered. In this way, more opportunity is given for the kV to be turned on when potential large displacement could happen. The higher probability of large displacement is because the time spent between each beam-on field is relatively long (typically 20-60 s). The method of the current invention leads to better motion detection performance compared to using only the 3D estimation method.

Figure 3:
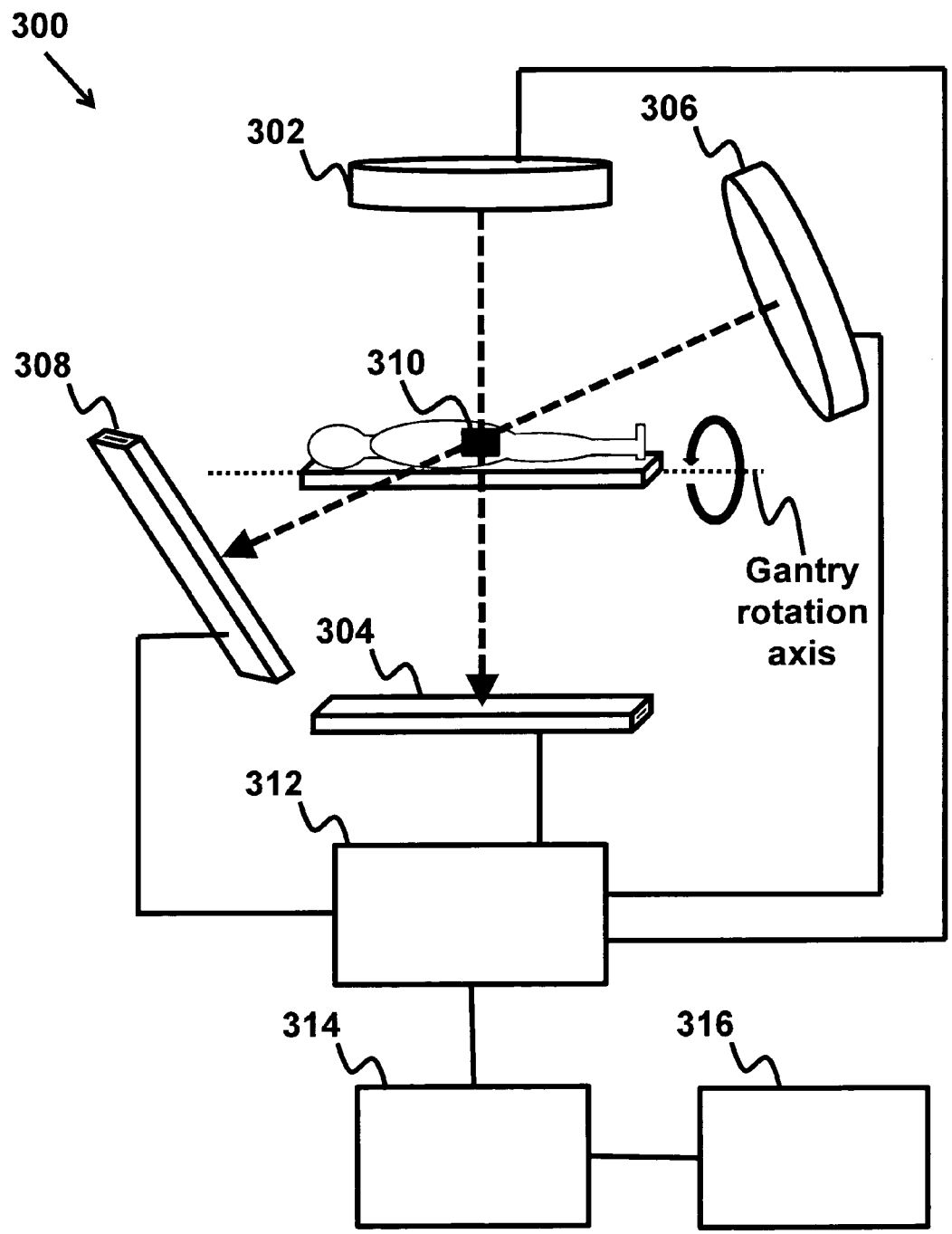
FIG. 3 shows a schematic drawing of one embodiment of the apparatus used for implementing the method for estimating fiducial position, according to one embodiment of the invention.

FIG. 3 shows a schematic drawing 300 of one embodiment of the apparatus used for implementing the method of monitoring intrafraction target motion during radiation therapy. As shown, a MV imaging source 302 and a MV imager 304 along with a KV imaging source 306 and a KV imager 308 are disposed to an initial 3D target 310 position. A 2D target position is monitored using the MV imaging process during the radiation therapy treatment delivery, where the 2D target position monitoring is in combination with an online-updated characterization of target 310 motion, where the online-updated characterization includes an image grabber 312, a computer 314 and display 316. The computer 314 operates appropriate software and algorithms to provide the 2D target position monitoring and the online-updating of the prostate motion to estimate if the target 310 has moved beyond a 3D threshold distance. The simultaneous MV imaging process and KV imaging process accurately determine a new 3D target 310 position for intrafraction motion compensation and for further 2D imaging by the MV imaging process. Another simultaneous MV imaging process and KV imaging process is initiated when the target 310 has potentially moved beyond the threshold distance as measured by the MV imaging process, where the intrafraction target motion monitoring is provided at a cost of ultralow patient imaging dose.

The present invention has now been described in accordance with several exemplary embodiments, which are intended to be illustrative in all aspects, rather than restrictive. Thus, the present invention is capable of many variations in detailed implementation, which may be derived from the description contained herein by a person of ordinary skill in the art. For example, it can also be used for conformal radiation therapy and volumetric modulated arc therapy; it can also be applied to intrafraction organ motion management for targets other than prostate.

All such variations are considered to be within the scope and spirit of the present invention as defined by the following claims and their legal equivalents.

What is claimed:

1. A method of monitoring intrafraction target motion during radiation therapy, comprising:
   a. using a first simultaneous Mega-Voltage (MV) imaging process and Kilo-Voltage (KV) imaging process to determine an initial 3D target position, wherein said MV imaging process comprises a MV imager and said KV imaging process comprises a KV imager;
   b. monitoring a 2D target position using said MV imaging process during a radiation therapy treatment delivery, wherein said 2D target position monitoring is in combination with an online-updated characterization of target motion, wherein said 2D target position monitoring and said online-updated characterization of said target motion are disposed to estimate if said target has moved beyond a 3D threshold distance; and
   c. using another said simultaneous MV imaging process and KV imaging process to accurately determine a new 3D target position for intrafraction motion compensation and for further 2D imaging by said MV imaging process, wherein said another simultaneous MV imaging process and KV imaging process is initiated when said target has potentially moved beyond said threshold distance as measured by said MV imaging process, wherein said intrafraction target motion monitoring is provided at a cost of ultralow patient imaging dose.

2. The method of monitoring intrafraction target motion of claim 1, wherein said MV imaging process is a cine MV imaging process.

3. The method of monitoring intrafraction target motion of claim 1, wherein said motion compensation comprises patient repositioning through automatic couch control or use of a dynamic multi-leaf collimator MLC.

4. The method of monitoring intrafraction target motion of claim 1, wherein said MV imaging process comprises a first viewing angle and said KV imaging process comprises a second viewing angle.

5. The method of monitoring intrafraction target motion of claim 1, wherein a confirmation request is generated when said target potentially moves beyond said threshold distance based on motion estimation.

6. The method of monitoring intrafraction target motion of claim 5, wherein said simultaneous MV imaging process and KV imaging process is initiated upon said confirmation request to confirm said target has moved beyond said threshold distance.

7. The method of monitoring intrafraction target motion of claim 5, wherein said target is repositioned when said confirmation request is confirmed.

8. The method of monitoring intrafraction target motion of claim 1, wherein said simultaneous MV imaging process and KV imaging process comprises a triangulation imaging of said target.

9. The method of monitoring intrafraction target motion of claim 1, wherein anterior-posterior motion is correlated with superoinferior motion of said target.

10. The method of monitoring intrafraction target motion of claim 1, wherein said threshold distance is at least 1 mm.

11. The method of monitoring intrafraction target motion of claim 1, wherein said KV imager comprises an x-ray KV imager.

12. The method of monitoring intrafraction target motion of claim 1, wherein said intrafraction motion tracking comprises said MV imager and another imaging modality.

* * * * *